United States Patent [19]

Grudzinskas et al.

[11] 4,141,914

[45] Feb. 27, 1979

[54] NOVEL 11-DEOXY-11-SUBSTITUTED PROSTAGLANDINS OF THE E AND F SERIES

[75] Inventors: Charles V. Grudzinskas, Garnerville, N.Y.; Martin J. Weiss, Oradell, N.J.

[73] Assignee: American Cyanamid Company, Stamford, Conn.

[21] Appl. No.: 274,559

[22] Filed: Jul. 24, 1972

[51] Int. Cl.² .................. C07C 121/46; C07C 121/48; C07C 69/74; C07C 61/38
[52] U.S. Cl. ........................... 260/464; 260/345.7 P; 260/345.8 P; 260/448.2 N; 260/456 R; 260/455 R; 542/429; 560/121; 562/503; 424/303; 424/304; 424/305

[58] Field of Search ............... 260/464, 345.7, 456 R, 260/448.2 N, 345.8, 240 R, 345.7 P, 345.8 P; 542/429

[56] References Cited

U.S. PATENT DOCUMENTS

| | | | |
|---|---|---|---|
| 3,723,423 | 3/1973 | Andersen et al. | 260/464 X |
| 3,751,463 | 8/1973 | Caton et al. | 260/464 X |

*Primary Examiner*—Joseph P. Brust
*Attorney, Agent, or Firm*—Edward A. Conroy, Jr.

[57] ABSTRACT

This disclosure describes 11-deoxy-11-substituted members of the $E_2$, $F_2$, $E_1$, $F_1$, dihydro $E_1$ and dihydro $F_1$ prostaglandin series which are useful as hypotensive agents and as anti-ulcer agents.

11 Claims, No Drawings

NOVEL 11-DEOXY-11-SUBSTITUTED PROSTAGLANDINS OF THE E AND F SERIES

BRIEF SUMMARY OF THE INVENTION

This invention relates to novel organic compounds of the prostaglandin class. In particular, the compounds of this invention are 11-deoxy-11-substituted members of the $E_2$, $F_2$, $E_1$, $F_1$, dihydro $E_1$ and dihydro $F_1$ prostaglandin series and may be represented by the following general formula:

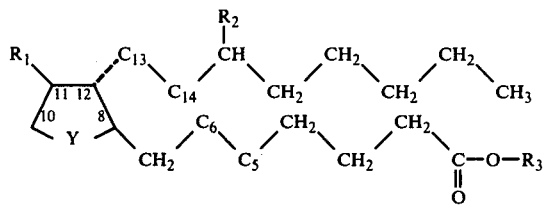

wherein $R_1$ is a member of the group consisting of the lower alkyl, lower 1-alkenyl, lower alkylthio, lower alkanoylthio, ω-di(lower alkyl)amino lower alkylthio, cyano, carboxamido, carboxylic acid and alkyl esters thereof, α-nitro lower alkyl, α,α-di(lower carboalkoxy) lower alkyl, α,α-dicarboxy lower alkyl, α-carboxy lower alkyl, di(lower alkyl)sulfonium halide, p-toluenesulfonylate or lower alkylsulfonylate, formyl, α,α-di(lower alkoxy)methyl and sulfhydryl radicals; $R_2$ is selected from the group consisting of the hydroxy, lower alkanoyloxy, lower alkylsulfonyloxy, tetrahydropyranyloxy, tri(lower alkyl)silyloxy, and lower alkyl radicals; $R_3$ is selected from the group consisting of hydrogen and an alkyl group having from 1 to 12 carbon atoms; Y is a divalent radical selected from the group consisting of:

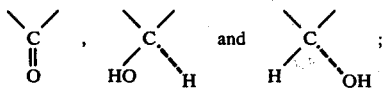

the moiety -$C_5$-$C_6$- is ethylene or cis-vinylene and the moiety -$C_{13}$-$C_{14}$- is ethylene or trans-vinylene with the proviso that when -$C_5$-$C_6$- is cis-vinylene then -$C_{13}$-$C_{14}$- must be trans-vinylene. Suitable lower alkyl, lower alkanoyl, and lower carboalkoxy groups contemplated by the present invention are those having up to four carbon atoms such as, for example, methyl, ethyl, isopropyl, sec-butyl, formyl, acetyl, propionyl, isobutyryl, carbomethoxy, carbethoxy, carbo-n-propoxy, etc. Halogen is exemplified by chloro, bromo, and iodo.

It is noteworthy that the $C_8$ and $C_{12}$ atoms in (I) are in the same optical configuration as are the corresponding atoms in the natural prostaglandins obtained from mammalian tissue. The $C_8$ and $C_{12}$ atoms of the novel compounds of this invention therefore also possess this configuration. The arrangement of the substituents on the $C_{15}$ atom in (I) is in the normal or (S) configuration, as is that found for the $C_{15}$ atoms of the natural prostaglandins of mammalian origin. However, the novel compounds of this invention also embrace compounds wherein the substituents on the $C_{15}$ atoms are in the (R) or "epi" configuration.

The $C_{11}$ substituents of the compounds of this invention can be introduced by a conjugate addition reaction with the $\Delta^{10}$-9-keto system of (I) or of the corresponding free 15-hydroxy derivative, or by a subsequent transformation of the new $C_{11}$-substituent. Among the reagents which can be utilized for conjugate addition are lithio di(lower alkyl) cuprates (e.g. lithio dimethylcuprate), lithio di(lower 1-alkenyl)cuprates, lower alkyl mercaptans, ω-di(lower alkyl)amino lower alkyl mercaptans, thio lower alkanoic acids, acetone cyanohydrin (for cyanide introduction), 1-nitro-lower alkanes, di(lower alkyl)malonates as well as di(lower alkyl)mono-lower alkyl substituted malonates. With the exception of the lithio di(lower alkyl)cuprates or lithio di(lower alkenyl)cuprates, the various reagents generally require conditions of alkaline or acid catalysis for effective conjugate additions. The appropriate conditions for each reagent are apparent from the examples included herein. Illustrative conjugate addition reactions are shown in Flowsheets A through E, wherein $R_4$ is a lower alkyl group or lower 1-alkenyl group, $R_5$ is a lower alkanoyl group, $R_6$ is hydrogen or a lower alkyl group, $R_7$ is a lower alkyl group, and X is halogen, p-toluenesulfonyloxy or lower alkylsulfonyloxy.

Also embraced within the scope of the present invention are the non-toxic, pharmaceutically acceptable salts of the novel compounds of the present invention when $R_3$ is hydrogen. The cations comprised in these salts include, for example, the non-toxic metal cations such as the sodium ion, potassium ion, calcium ion, and magnesium ion as well as the organic amine cations such as the tri(lower alkyl)amine cations (e.g., triethylamine), procaine, and the like.

The novel compounds of the present invention are obtainable as yellow oils having characteristic absorption spectra. They are relatively insoluble in water but are relatively soluble in common organic solvents such as ethanol, ethyl acetate, dimethylformamide, and the like. The cationic salts of the compounds when $R_3$ is hydrogen are, in general, white to yellow crystalline solids having characteristic melting points and absorption spectra. They are relatively soluble in water, methanol, and ethanol but are relatively insoluble in benzene, diethyl ether, and petroleum ether.

DETAILED DESCRIPTION OF THE INVENTION

The compounds of this invention can be prepared from the methyl ester (I) of 15-O-acetylprostaglandin-$A_2$ which can be isolated from the gorgonid *Plexaura homomalla* (esper), a sea coral found in the Caribbean Sea. The isolation of the corresponding 15-epi derivative from this gorgonid is described by A. J. Weinheimer and R. L. Spraggins in *Tetrahedron Letters*, No. 59, 5185 (1969).

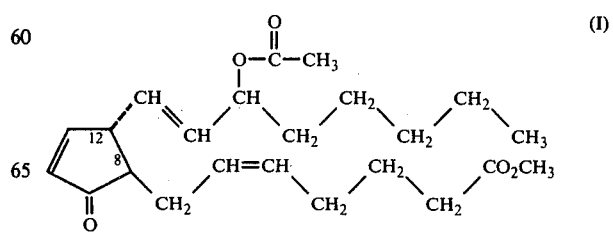

FLOWSHEET A
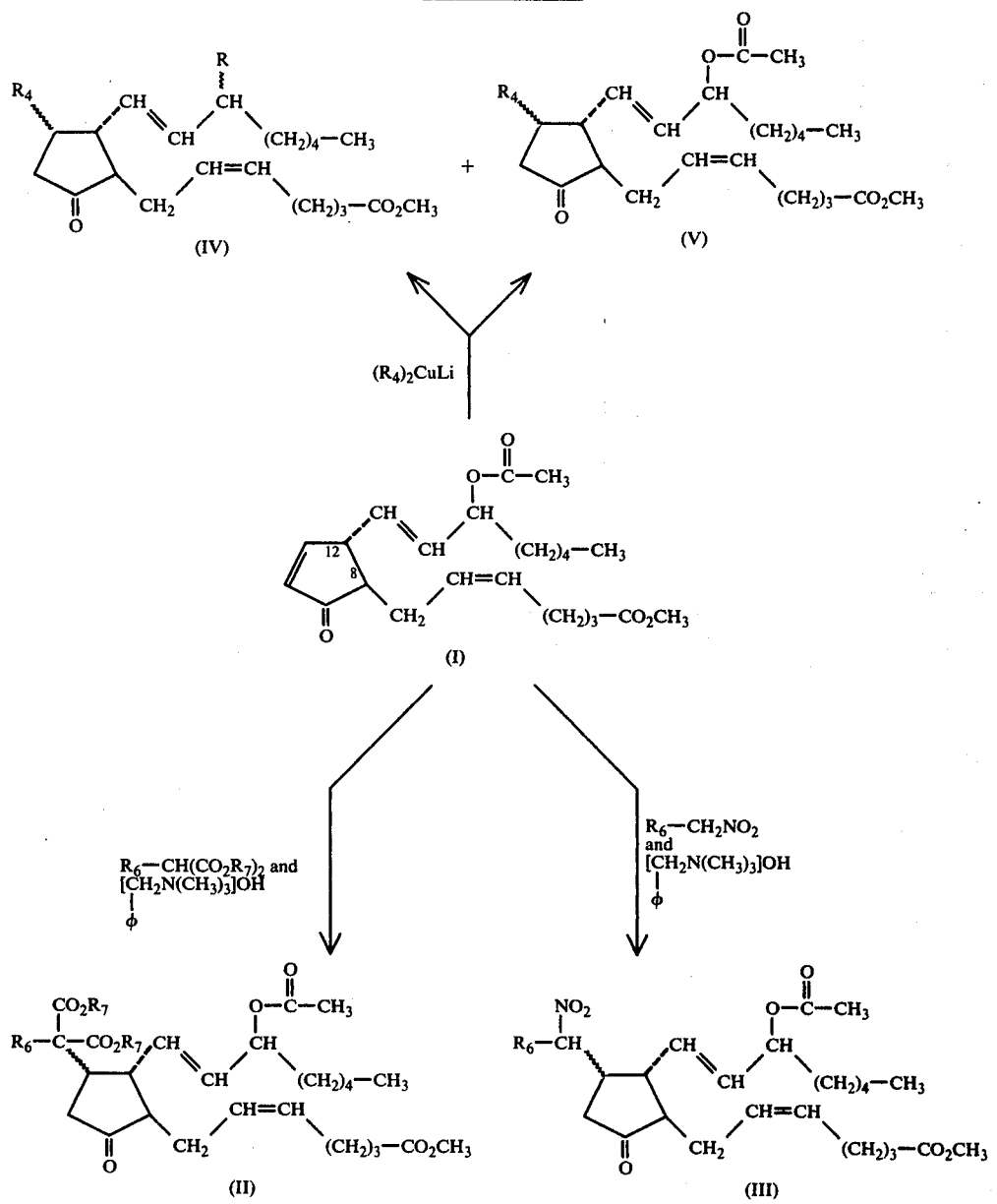
FLOWSHEET B
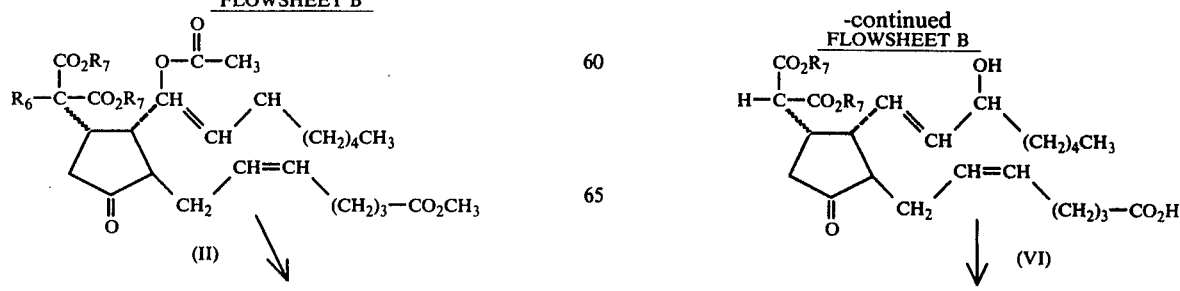

-continued
FLOWSHEET B
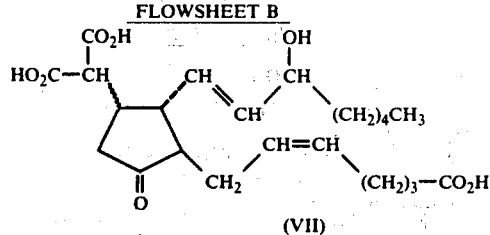
(VII)
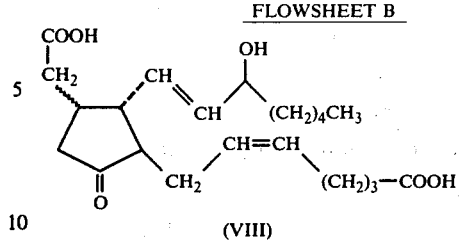
(VIII)
FLOWSHEET C
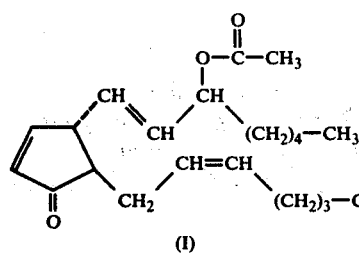
(I)
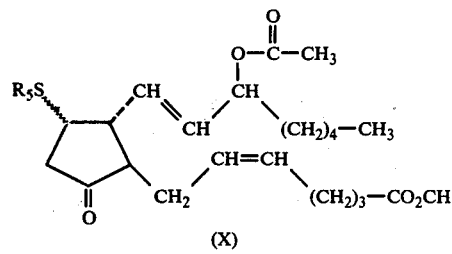
(X)
R₄SH
KHCO₃
R₅SH
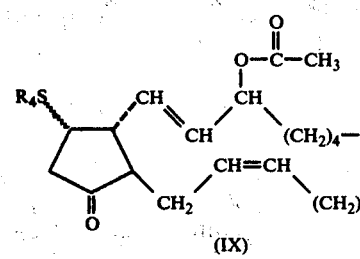
(IX)
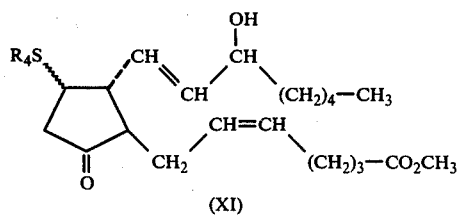
(XI)
R₄SH
K₂CO₃
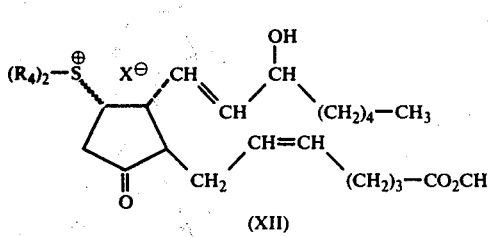
(XII)
R₄—X 7
FLOWSHEET D
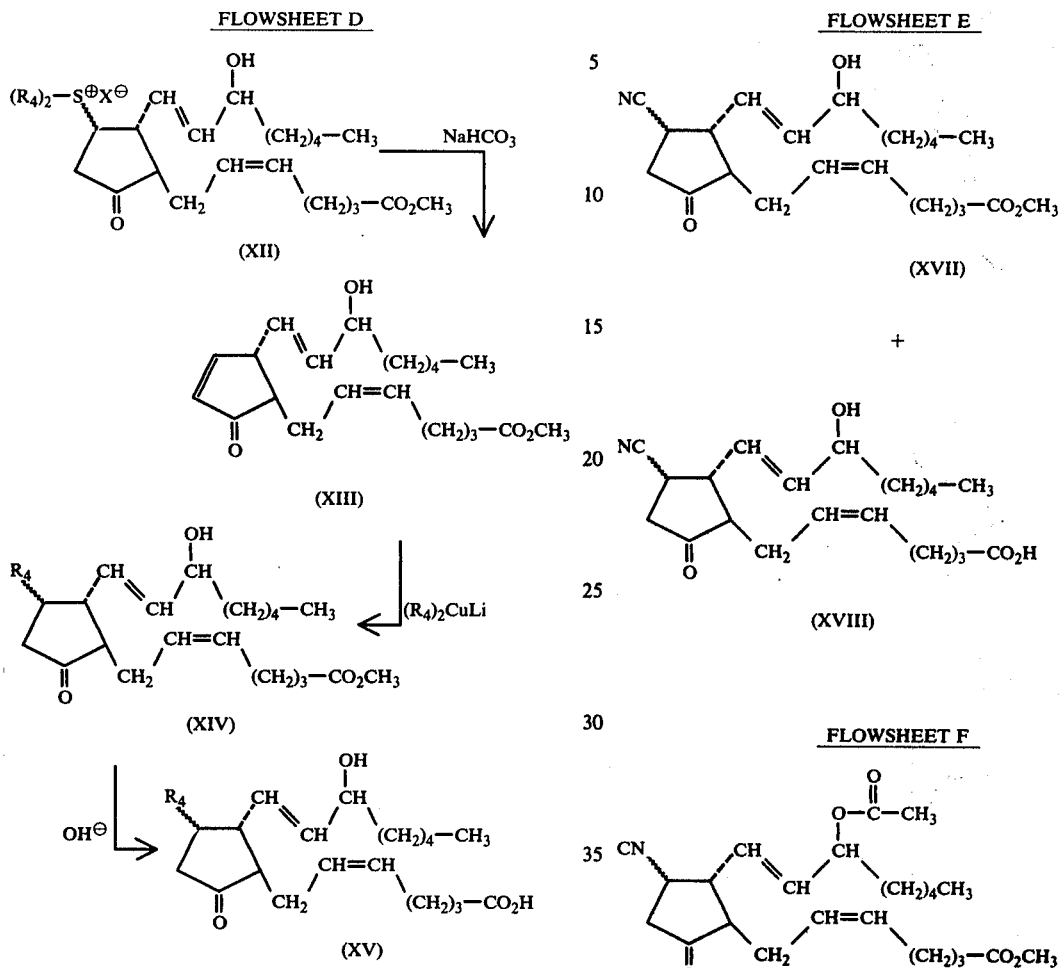
FLOWSHEET E
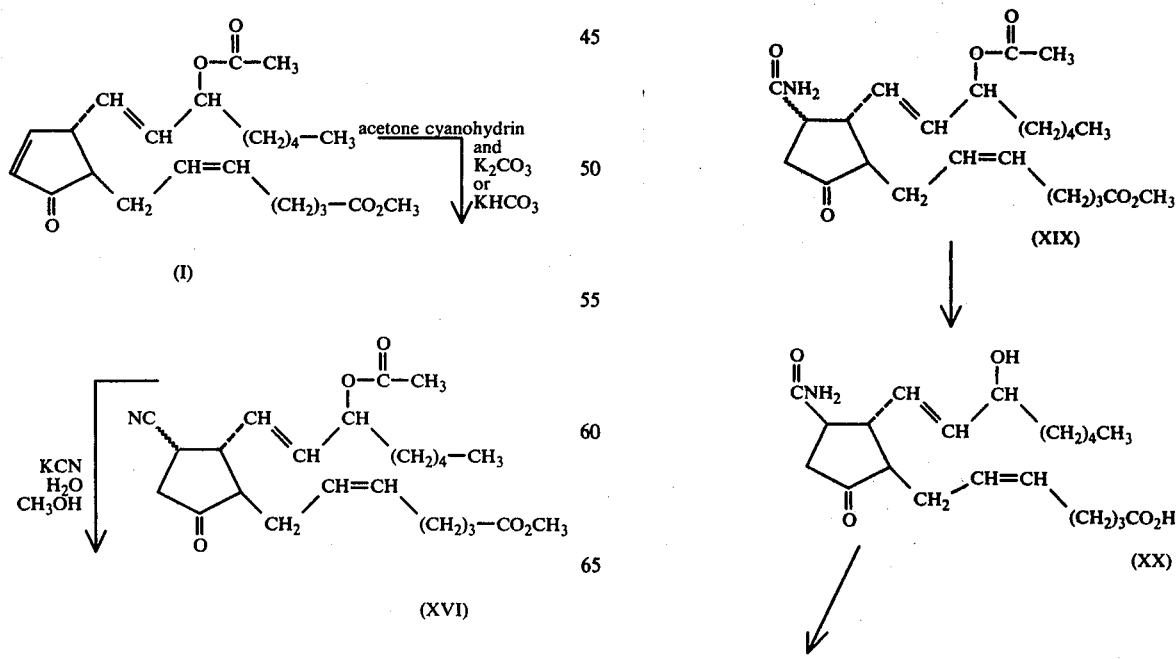

-continued
FLOWSHEET F

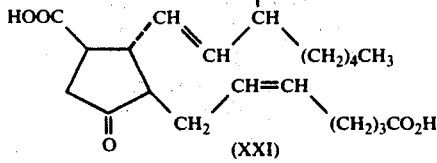

The preparation of the free 15-hydroxy derivative (XIII) of (I) is difficult to achieve directly by the usual acid-or-base-catalyzed conditions of hydrolysis. Under these circumstances (I or XIII) is too unstable and rearrangement to the prostaglandin $B_2$ system (XXII) and-/or a novel triene (XXIII) is observed.

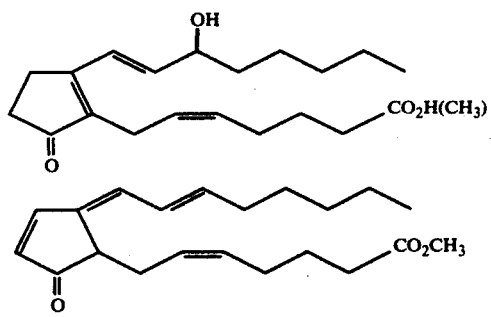

In order to prepare the free 15-hydroxy derivative (XIII) we have developed a convenient and novel procedure, which we consider to be a part of this invention. This procedure involves the conjugate addition to the diester (I) of an alkyl mercaptan (e.g., methyl mercaptan or ethyl mercaptan) to give the 11-alkylthio derivative (IX). Saponification of diester (IX) with potassium carbonate in the presence of excess alkyl mercaptan then procedes smoothly to provide the free 15-ol-11-alkylthio derivative (XI). The presence of alkyl mercaptan during this treatment presumably maintains the 11-alkylthio group, which otherwise would be eliminated under these conditions to give the $\Delta^{10}$-9-keto system, unstable to saponification conditions. Thus, in effect this procedure protects this latter system during saponification. The $\Delta^{10}$-function can then be regenerated under conditions to which it is stable by enhancing the leaving potential of the alkylthio group by conversion to a sulfonium salt (XII), which is eliminated readily with sodium bicarbonate to give the methyl ester of $PGA_2$ (XIII). The overall yield for the conversion of (I) to (XIII) is usually quite high, on the order of 70–85%, and several of the steps can be combined.

The free 15-ol (XIII) is a useful intermediate. For example, treatment with lithium dialkyl cuprates provides high yields of the 11-lower alkyl derivatives (XIV) without involvement of the hydroxy function. When the same reagent is used to treat the diester (I), the 15-acetoxy function becomes involved and a substantial portion of the product is the 11,15-di(lower alkyl) derivative (IV).

Other novel compounds embraced by this invention can be prepared by further transformations of the above-described conjugate addition products. Thus, for example, hydrolysis of the malonate addition product (VI) furnishes the 11-(α,α-dicarboxy lower alkyl) derivative (VII), decarboxylation of which provides the 11-(α-carboxy lower alkyl) derivative (VIII). Treatment of the 11-cyano derivative (XVI) with alkaline hydrogen peroxide gives the 11-carboxamido diester (XIX), which on mild hydrolysis (three equivalents of potassium hydroxide, three hours, ambient temperature) gives the corresponding 15-hydroxy carboxylic acid (XX). Vigorous alkaline hydrolysis of (XX) then yields the 11-carboxylic acid derivatives (XXI).

The 9-carbonyl function in the 11-substituted derivative obtained after conjugate addition can be reduced to an alcohol function. When this reduction is carried out with sodium borohydride a mixture of 9α- and 9β-hydroxy products is obtained. When the reduction is carried out with lithium perhydro-9β-borophenalylhydride (XXIV) [H. C. Brown and W. C. Dickason, *Journ. Amer. Chem. Soc.*, 92, 709 (1970)] the product is predominately, if not completely, the 9α-hydroxy derivative.

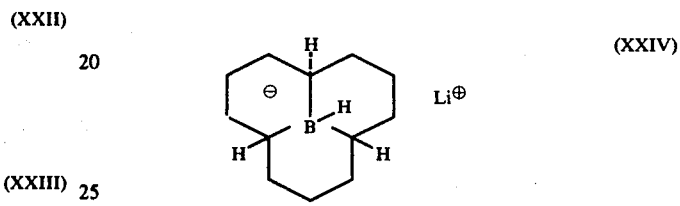

Hydrolysis of the 11-substituted 15-O-acetyl derivatives under mild conditions, as for example, the conversion of (IX) to (XI) provides the corresponding 15-hydroxy methyl ester. Similarly, treatment of (XVI) with aqueous methanolic potassium cyanide provides the 11-cyano-15-hydroxy-ester (XVII) as well as the corresponding acid (XVIII). Alkaline saponification of the esters provides the corresponding acids (e.g., XIV→XV). When the 11-substituent is subject to elimination reactions under such conditions, as for example with the 11-alkylthio derivatives (XI), the desired 11-substituted free 15-hydroxy carboxylic acid can be prepared by the appropriate conjugate addition reaction with the known $PGA_2$(XXV).

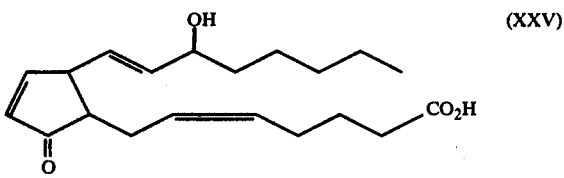

Esterification of the free 15-hydroxy function as well as of the free carboxylic acid function by the usual procedures provides the other ester derivatives of this invention.

The initial products of this invention have the 15-oxy function in the (S) or "normal" configuration. Conversion to the alternate (R) or "epi" configuration can be accomplished by two procedures, illustrated below in Flowsheet G for the 11-methyl series.

Treatment of (XXVIII) with a solution of sodium formate in formic acid induces racemization of the 15-oxy function and a mixture of the 15(R) and 15(S) formyloxy derivatives (XXVI) and (XXVII) are obtained. Separation of this mixture by chromatography provides the individual components and formate hydrolysis gives the original 15(S)-ol (XXVIII) and the inverted 15(R)-ol (XXXI).

Epimerization of the 15(S)-ol (XXVIII) can be accomplished by conversion to a sulfonyloxy derivative (XXIX), such as methanesulfonyloxy, by treatment with methanesulfonic acid anhydride at low temperatures in the presence of an organic base such as triethylamine. The sulfonyloxy derivative (XXIX) is then treated with tetraethyl ammonium formate in a suitable organic solvent to produce the inverted 15(R)-formyloxy derivative (XXVII). Formate hydrolysis then provides the 15(R)-alcohol (XXXI).

The 15(R) derivatives can also be obtained by conjugate addition reactions with the 15(R) epimer of diester (I) or with the corresponding 15(R) free carboxylic acid 15-O-acetylate, or with the corresponding 15(R)-hydroxy free carboxylic acid, also isolable from *Plexaura homomalla* (A. J. Weinheimer R. L. Spraggins loc. cit.).

nation as just described or by reduction of the 9-carbonyl function of the corresponding E compound).

Alternatively, the various 11-substituted derivatives of this invention in the 11-deoxy-prostaglandin-$E_1$ series can be prepared by conjugate 1,4-addition to either prostaglandin $A_1$ or THE METHYL ESTER OF PROSTAGLANDIN $A_1$ [NETHERLANDS PATENT APPLICATION No. 6,611,478; *Chem. Abst.* 68, 2633m, (1968)]. The 11-substituted derivatives of this invention in the 11-deoxy-13-dihydroprostaglandin $E_1$ series can be prepared by conjugate 1,4-addition to either 13-dihydroprostaglandin A, or the methyl ester of 13-dihydroprostaglandin $A_1$ prepared by the acid-catalyzed elimination of water [procedure described by E. J. Corey et al. in *Jour. Amer. Chem. Soc.*, 90, 3247

FLOWSHEET G

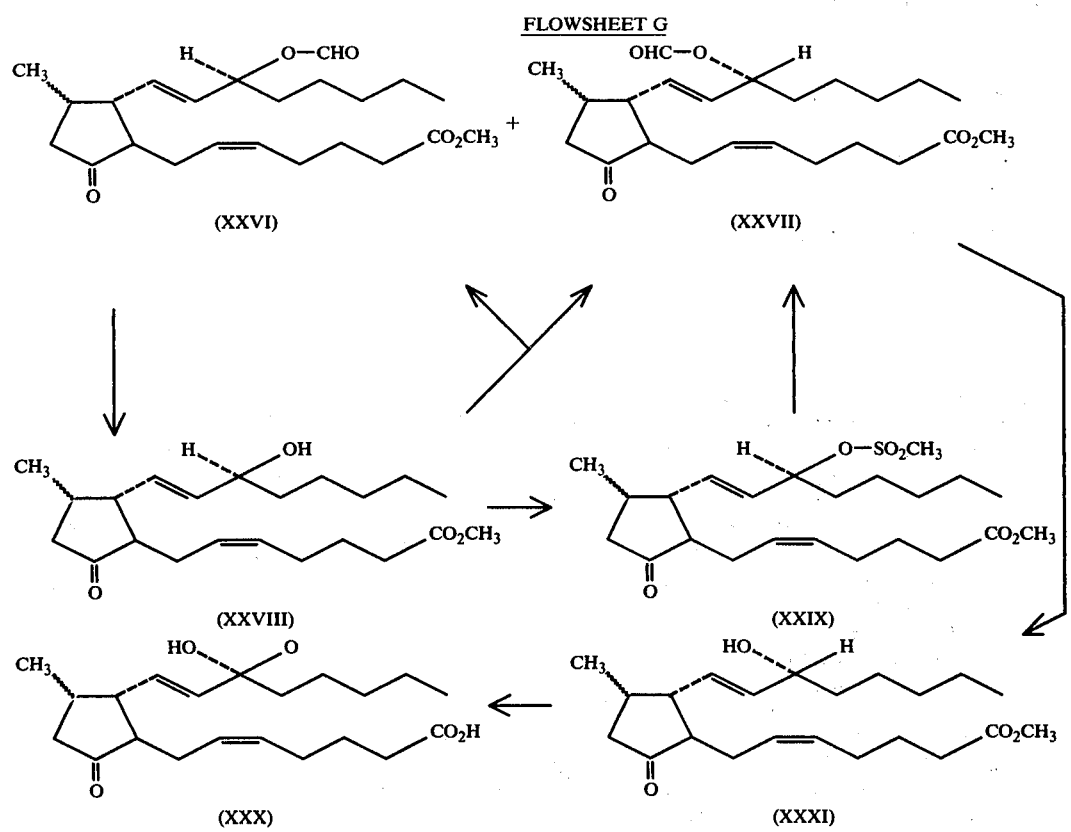

(1968)] from 13-dihydroprostaglandin $E_1$ [O. Korver, *Rec. Trav. Chim.*, 88, 1070 (1969)] or the methyl ester of 13-dihydroprostaglandin $E_1$ [B. Samuelsson and G. Stallberg, *Acta. Chem. Scand.*, 17, 810 (1963)], respectively, in accordance with the considerations noted hereinabove for conjugate addition with members of the prostaglandin $A_2$ series.

The configuration of the various substituents at $C_{11}$ is not known with certainty. In at least one instance, cyano, it appears that a mixture of two epimeric 11-cyano derivatives was obtained. In other instances, as with the 11-alkylthio derivatives and the 11-methyl derivatives, the available evidence indicates that the products consist of only one epimer, or at the least one epimer in predominant amount; the evidence and theoretical considerations leads to the assignment to these epimers of the 11-normal configuration, i.e., a trans-relationship between the 11-substituent and the adjacent side-chain.

The novel compounds of this invention can be converted to other novel derivatives of the 11-deoxy prostaglandin $E_1$ and $F_1$ series by preferential reduction of the $\Delta^5$ cis-double bond. This can be achieved by careful catalytic hydrogenation in the presence of a metal catalyst such as palladium-carbon or $RhCl\text{-}[P(C_6H_5)_3]_3$ or by use of diimide. Selectivity for the reduction of the $\Delta^5$ bond can be enhanced by first converting the 15-ol to a derivative which sterically hinders the approach to the competing $\Delta^{13}$ double bond. Useful 15-hydroxy derivatives for this purpose include the tetrahydropyranyl derivatives and the dimethylisopropylsilyl ether.

This invention also includes the novel 11-substituted derivatives of 13-dihydro-11-deoxy-prostaglandin $E_1$ and $F_1$. These compounds, in which both the $\Delta^5$ and $\Delta^{13}$ double bonds are saturated, can be prepared by catalytic hydrogenation in the usual manner of the corresponding members of the $E_2$ or $F_2$ series. (F derivative of the 1 or dihydro-1 series can be prepared from the corresponding $F_2$ derivative by partial or full hydroge- The compounds of this invention are useful as protective agents against the ulcerogenic and gastrointestinal effects induced by certain otherwise valuable pharmaceutical agents, particularly non-steroidal anti-inflammatory agents such as indomethacin, phenylbutazone, and aspirin. Indicative of the serious nature of this problem are the following statements concerning indomethacin (Indocin ®) taken from *Physician's Desk Reference* 1972 (Medical Economics Inc., Oradell, New Jersey), p. 964.

"Gastrointestinal Effects:

Because of the occurrence and, at times, severity of gastrointestinal reactions to INDOCIN, the prescribing physician must be continuously alert for any sign or symptom signalling a possible gastrointestinal reaction. The risks of continuing INDOCIN therapy in the face of such symptoms must be weighed against the possible benefits to the individual patient. The gastrointestinal effects may be reduced by giving the drug immediately after meals, with food, or with antacids. As advancing years appear to increase the possibility of adverse reactions, INDOCIN should be used with concomitantly greater care in the aging."

"Gastrointestinal Reactions:

Single or multiple ulcerations, including perforation and hemorrhage of the esophagus, stomach, duodenum or small intestines. Fatalities have been reported to occur in some instances. Gastrointestinal bleeding without obvious ulcer formation. Perforation of pre-existing sigmoid lesions (diverticulum, carcinoma, etc.). Increased abdominal pain in ulcerative colitis patients or the development of ulcerative colitis and regional ileitis have been reported to occur rarely. Gastritis may persist after the cessation of the drug. Nausea, vomiting, anorexia, epigastric distress, abdominal pain and diarrhea."

It is further to be noted that although prostaglandins in general are not effective when administered by the oral route, the compounds of this invention are effective orally. The assay to determine the protective effect of these compounds is carried out in the following manner.

Rats were starved for 48 hours (water was given ad libitum). Indomethacin (20 mg./kg. of body weight) was administered by the subcutaneous route and one-half the dose of the test compound was administered by gavage at the same time. After three hours, the second half of the test compound was administered, also be gavage. Five hours after the administration of indomethacin the animals were decapitated and the stomachs removed. The stomachs were washed with distilled water, blotted on gauze, cut along the larger curvature, and the contents rinsed with distilled water. The stomachs were spread out, pinned on a cork and visualized under magnifying glass for ulcers. The criteria for scoring of ulcers was as previously reported. [Abdel-Galil et al. *Brit. J. Pharmac. Chemotherapy* 33:1-14 (1968)].

Score

0 — Normal stomach
1 — Petechial hemorrhage of pin point ulcers
2 — 1 or 2 small ulcers
3 — Many ulcers, a few large
4 — Many ulcers, mainly large Control animals treated with indomethacin but not test compound consistently give scores of about 2.5-3.5. Control animals treated with neither indomethacin not test compound give scores of about 0.5-0.8. The results obtained in this assay with typical compounds of the present invention are set forth in the table below. Compounds diminishing the control ulcer score by 0.5 unit or more are considered to be active.

TABLE I

| Compound | Total oral dose; mg./kg. of body weight | SCORE Treated Animals | SCORE Controls |
|---|---|---|---|
| $11\alpha/\beta$-cyano-11-deoxyprostaglandin-$E_2$-methyl ester | 25 | 1.3 | 2.7 |
| $11\alpha/\beta$-cyano-11-deoxyprostaglandin-$E_2$ | 12.5 | 1.2 | 2.5 |
| $11\alpha$-nitromethyl-11-deoxyprostaglandin-$E_2$ | 100 | 1.0 | 3.2 |
| $11\alpha$-methylthio-11-deoxyprostaglandin-$E_2$ 15-O-acetate methyl ester | 50 | 2.0 | 2.7 |
| $11\alpha$-methyl-11-deoxyprostaglandin-$E_2$ | 6.25 | 2.5 | 3.0 |
|  | 12.5 | 2.0 | 3.0 |
|  | 25.0 | 1.7 | 3.0 |
| $11\alpha$-carboxamido-11-deoxyprostaglandin-$F_{2\alpha}$ | 50 | 2.3 | 3.2 |
| $11\alpha/\beta$-cyano-11-deoxyprostaglandin-$E_2$ 15-O-acetate methyl ester | 50 | 1.3 | 3.0 |
|  | 12.5 | 2.0 | 2.7 |
| $11\alpha$-methyl-11-deoxy-13-dihydroprostaglandin-$E_1$ | 50 | 1.7 | 3.0 |
|  | 12.5 | 2.3 | 3.0 |
| $11\alpha$-methyl-11-deoxyprostaglandin-$F_{2\alpha}$ | 25 | 1.8 | 2.7 |
| $11\alpha,15$-dimethyl-11,15-bis-deoxyprostaglandin-$E_2$ | 50 | 2.2 | 3.0 |
| $11\alpha$-cyano-11-deoxy-prostaglandin-$F_{2\alpha}$ | 25 | 1.3 | 2.8 |

The novel compounds of the present invention are effective inhibitors of gastric acid secretion and of ulcer development in experimental animals, and thus are potentially valuable as agents for the control of gastric acid secretion and of gastric erosion and as anti-ulcer agents. Gastric acid secretion inhibitory action is usually measured by the "Shay rat" procedure[1,2] with some modifications as follows.

The rats (male, CFE strain) were starved for 48 hours (water was given ad libitum) to permit evacuation of stomach contents. On the morning of the experiment, under ether anesthesia, the abdominal region was shaved and a midline incision (1-1½") was made with a scapel. With the help of a closed curved hemostate the duodenum was picked up. Upon getting the duodenum into view, fingers were used to pull the stomach through the opening, the stomach was then gently manipulated with fingers to rid stomach of air and residual matter which were pushed through the pylorus. Two 5 inch sutures were drawn under the pyloric-duodenal puncture. A ligature, at the juncture, was formed with one of the threads. The second ligature was also formed but not tightened.

The test compound or the vehicle, usually 1 ml./100 g. body weight, were injected into the duodenum as close as possible to the first ligature. After injection the second ligature was tightened below the injection site to minimize leakage. The stomach was placed back through the opening into the abdominal cavity, the area of incision was washed with saline and the incision was closed with autoclips. (Occasionally, instead of an intraduodenal injection, animals were dosed by the oral or subcutaneous route. In the latter case, dosing was done thirty to sixty minutes before the operation.)

Three hours later, the rats were decapitated and exanguinated, taking care that blood did not drain into the esophagus. The abdominal cavity was exposed by cutting with scissors and the esophagus close to the stomach was clamped off with a hemostat, the stomach was removed by cutting above the hemostat (the esophagus was cut) and between the two sutures. Extraneous tissue was removed, the stomach washed with saline and blotted on gauze. A slit was carefully made in the stomach which was held over a funnel and the contents were collected in a centrifuge tube. The stomach was further cut along the outside edge and turned inside out. Two ml. $H_2O$ were used to wash the stomach contents into the respective centrifuge tube. The combined stomach contents and wash were then centrifuged out for 10 min. in the International Size 2 Centrifuge (setting at 30). The supernatant was collected, volume measured and recorded, 2 drops of a phenylphthalein indicator (1% in 95% ethanol) were added and the solution was titrated with 0.02N NaOH (or with 0.04N NaOH when large volumes of stomach contents were encountered) to pH 8.4 (because of usual coloring of the stomach contents, phenolphthalein was only used to permit visual indication that the end point was near) and the amount of acid present was calculated.

Compounds inducing inhibition of gastric acid secretion of 20% or more were considered active. In a representative operation, and merely by way of illustration, the results obtained with this assay with typical compounds of the present invention are given in Table II below.

TABLE II

| Compound | Intraduodenal dose, mg./kg. of body weight | Percent Inhibition |
|---|---|---|
| 11α/β-cyano-11-deoxyprostaglandin-$E_2$ 15-O-acetate methyl ester | 25 | 51 |
| 11α/β-cyano-11-deoxyprostaglandin-$E_2$ methyl ester | 50 | 33 |
| 11α/β-cyano-11-deoxyprostaglandin-$E_2$ | 50 | 79 |
| | 25 | 31 |
| 11α-cyano-11-deoxyprostaglandin-$F_{2\alpha}$ | 50 | 43 |
| 11α-ethylthio-11-deoxyprostaglandin-$E_2$ 15-O-acetate methyl ester | 50 | 27 |
| 11α-methylthio-11-deoxyprostaglandin-$E_2$ 15-O-acetate methyl ester | 50 | 35 |
| 11α-methyl-11-deoxyprostaglandin-$E_2$ | 50 | 63 |
| 11α-methyl-11-deoxyprostaglandin-$F_{2\alpha}$ | 50 | 70 |
| 11α-methyl-11-deoxy-13-dihydro-prostaglandin-$E_1$ | 50 | 45 |
| 11α-methyl-11-deoxyprostaglandin-$E_2$ 15-O-acetate methyl ester | 50 | 63 |
| 11α,15-dimethyl-11,15-bisdeoxy-prostaglandin-$E_2$ methyl ester | 50 | 40 |
| 11α,15-dimethyl-11,15-bisdeoxy-prostaglandin-$E_2$ | 50 | 60 |
| 11α-carboxamido-11-deoxyprostaglandin-$E_2$ | 50 | 27 |
| 11α-carboxamido-11-deoxyprostaglandin-$F_{2\alpha}$ | 50 | 27 |
| 11α-nitromethyl-11-deoxyprostaglandin-$E_2$ | 100 | 74 |
| 11α-vinyl-11-deoxyprostaglandin-$E_2$ | 50 | 59 |
| 11α-methylthio-11-deoxyprostaglandin-$E_2$ methyl ester | 100 | 55 |

Bronchodilator activity was determined in guinea pigs against bronchospasms elicited by intravenous injections of 5-hydroxytryptamine, histamine or acetylchlorine by the Konzett procedure. [See J. Lulling, P. Lievens, F. El Sayed and J. Prignot, *Arzneimittel-Forschung*, 18, 995 (1968).]

In the Table which follows bronchodilator activity for representative compounds of this invention against one or more of the three spasmogenic agents is expressed as an $ED_{50}$ determined from the results obtained with three logarithemic cumulative intravenous doses.

TABLE III

Bronchodilator Activity (Konzett Assays) $ED_{50}$, mg./kg.

| Compound | Spasmogenic Agent | | |
|---|---|---|---|
| | 5-hydroxy-tryptamine | histamine | acetyl-choline |
| 11α-methyl-11-deoxy-13-dihydroprostaglandin-$E_1$ | | | 0.773 |
| 11β-cyano-11-deoxyprostaglandin-$F_{2\beta}$ | | 1.66 | |
| 11α-methyl-11-deoxyprostaglandin-$F_{2\alpha}$ | 0.038 | 0.013 | |
| 11α-methyl-11-deoxyprostaglandin-$E_2$ | 0.0022 | 0.050 | 1.19 |
| 11α,15-dimethyl-11,15-bis-deoxyprostaglandin-$E_2$ | 18.1 | | |
| 11-cyano-11-deoxy-prostaglandin-$E_2$ | .0036 | 0.0054 | 0.091 |

The novel compounds of the present invention also have potential utility as hypotensive agents, antimicrobial agents, anticonvulsants, abortifacients, agents for the induction of labor, agents for the induction of menses, fertility-controlling agents, central nervous system regulatory agents, salt and water-retention regulatory agents, diuretics, fat metabolic regulatory agents, serum-cholesterol lowering agents and as inhibitors of platelet aggregation. Certain of the novel compounds of this invention possess utility as intermediates for the preparation of other of the novel compounds of this invention.

This invention will be described in greater detail in conjunction with the following specific examples.

EXAMPLE 1

Isolation of the methyl ester of 15-O-acetylprostaglandin $A_2$ from *Plexaura Homomalla* (esper)

Specimens of *Plexaura Homomalla* (esper) are collected in Puerto Rican waters, air dried and stored under a nitrogen atmosphere at 0° C. The cortex is removed, ground and extracted with isomeric hexanes. The organic solvent is evaporated in vacuo to afford a prostaglandin containing residue. The residue is dissolved in nitromethane and extracted with isomeric hexanes. The nitromethane solution is evaporated to give a residue that is approximately 50% by weight of the residue prior to the nitromethane treatment. This process, in addition to the removal of unwanted materials, (largely fatty esters), also has the benefit of selectively removing the sterols that have nearly the same rf index on silica gel as that of the methyl ester of 15-O-acetylprostaglandin $A_2$.

Purification of the residue via dry column chromatography using acid washed silica gel and 5% ethyl acetate as elutant yields the 15-O-acetyl-prostaglandin $A_2$ methyl ester and prostaglandin $A_2$ methyl ester. The combined yield of the two prostaglandins is 1–2%.

The configuration of the C-15 carbon is established by degradation with ozone followed by chromic acid oxidation to yield α-acetoxyheptanoic acid. The configuration of the acetoxy grouping is established by comparison of the circular dichromism curves of α-acetoxyheptanoic acid and D-α-acetoxypropanoic acid prepared from the calcium salt of D-lactic acid (R-configuration). Compounds of like configuration will display curves of the same sign. D-α-acetoxypropanoic acid displays a negative circular dichromism curve whereas the degradation product, α-acetoxyheptanoic acid gives a positive circular dichromism curve.

EXAMPLE 2

Preparation of 11-deoxy-11α-ethylthio-15-O-acetyl prostaglandin $E_2$ methyl ester — Method A To a solution of 7.23 gm. of the methyl ester of 15-O-acetyl-prostaglandin $A_2$ in a mixture of 15 ml. ethanethiol, 15 ml. of tetrahydrofuran and 15 ml. of methanol is added 1.8 ml. of aqueous 5% sodium bicarbonate. The solution is stirred for twenty minutes and is evaporated in vacuo at 30° C. to a paste. To the paste is added 25 ml. ether and 10 ml. of water. The ether is separated and washed with brine. The aqueous layer is extracted with ether and the ether is washed with brine and the ether extracts are combined, dried with magnesium sulfate, and evaporated in vacuo to afford 8.375 gm. of 11-deoxy-11α-ethylthioprostaglandin $E_2$ methyl ester as an oil; λ max: 1740 $cm^{-1}$ (saturated ketone and esters), 1225 $cm^{-1}$ (acetate); $[\alpha]_D^{25} = -59.67°$ (C = 0.481 chloroform).

EXAMPLE 3

Preparation of 11-deoxy-11α-methylthioprostaglandin $E_2$ — Method B

A solution of prostaglandin $A_2$ is treated as in Example 2 except that one equivalent of sodium bicarbonate in water is added before the addition of a catalytical amount of 5% aqueous sodium bicarbonate. In addition, the solution is acidified with a sodium biphosphate buffer prior to the extraction with ether to yield 11-deoxy-11α-methylthioprostaglandin $E_2$ after evaporation in vacuo of the organic solvents.

EXAMPLE 4

Conversion of 15-O-acetylprostaglandin $A_2$ methyl ester to prostaglandin $A_2$ methyl ester To a 0° C. solution containing 12.15 gm. of 15-O-acetylprostaglandin $A_2$ methyl ester in 50 ml. of methanethiol and 100 ml. of methanol is added a small amount of potassium carbonate. The solution is stirred 30 minutes and 75 ml. of methanol and 8.55 gm. of potassium carbonate is added. The flask is tightly stoppered, secured with rubber bands and stirred at room temperature for two weeks. The solution is cooled in an ice bath and poured into 350 ml. of ether and 500 ml. of ice water. The aqueous layer is extracted with ether and the combined ether extracts are washed with brine and dried with magnesium sulfate. The ether is evaporated in vacuo and the residue is dissolved in 100 ml. of methanol and filtered through celite to remove stopcock crease. The methanol is evaporated in vacuo to afford 11.67 gm. of crude 11-deoxy-11α-methylthioprostaglandin $A_2$ methyl ester as an oil.

To a solution of 11.67 gm. of crude 11-deoxy-11α-methylthioprostaglandin $A_2$ methyl ester in a solution of 60 ml. tetrahydrofuran, 30 ml. of methanol and 25 ml. of iodomethane is added 70 ml. of a 5% aqueous sodium bicarbonate solution. The resulting solution is stirred vigorously and heated under reflux for four hours to form 11-deoxy-11α-dimethylsulfonium iodide prostaglandin $A_2$ methyl ester which is decomposed in solution to afford prostaglandin $A_2$ methyl ester.

The solution is cooled and added to 200 ml. of ether and 100 ml. of water. The aqueous layer is extracted with ether and the ether extracted are combined, washed with brine, dried with magnesium sulfate and evaporated in vacuo to afford 10.63 gm. of the crude prostaglandin $A_2$ methyl ester as an oil.

The oil is purified by dry column chromatography using acid washed silica gel. The material in methylenechloride is placed onto a 62" × 3" flat diameter nylon tube containing the acid washed silica. The column is developed with ether and is then cut up into 10 equal sections. Sections 6, 7 and 8 are combined and the product is eluted from the silica gel with 20% methanol in chloroform.

Evaporation in vacuo of the solvents affords 8.64 gm. (80%) of prostaglandin $A_2$ methyl ester; λ max 1735 $cm^{-1}$, 1710 $cm^{-1}$, 1660 $cm^{-1}$, 3400 $cm^{-1}$; $[\alpha]_D^{25} = +137.5$ (C = 0.4, chloroform).

Elution of the material from sections 9 and 10 of the column in like fashion yields 1.2 gm. of the starting 15-O-acetyl prostaglandin methyl ester.

Substitution of ethanethiol for methanethiol in the above procedure results in the formation of 11-deoxy-11α-ethylthioprostaglandin $A_2$ methyl ester and 11-deoxy-11α-(ethyl methyl sulfonium iodide) prostaglandin $A_2$ methyl ester as intermediates in the preparation of prostaglandin $A_2$ methyl ester.

EXAMPLES 5-12

Treatment of the following A type prostaglandins with the following alkyl mercaptans in the manner of Example 2 (Method A) or Example 3 (Method B) is productive of the 11α-alkylthioprostaglandins (E type) of the table.

| Example | Starting Prostaglandin | Alkyl Mercaptan | Method | Product 11α-alkylthio-prostaglandin E |
|---|---|---|---|---|
| 5 | 15-O-acetyl prostaglandin $A_2$ methyl ester | ethanethiol | A | 11-deoxy-11α-ethyl thioprostaglandin $E_2$ methyl ester |
| 6 | prostaglandin $A_2$ | methanethiol | B | 11-deoxy-11α-methylthioprostaglandin $E_2$ |
| 7 | prostaglandin $A_2$ | ethanethiol | B | 11-deoxy-11α-ethylthioprostaglandin $E_2$ |
| 8 | prostaglandin $A_2$ | 2-propanethiol | B | 11-deoxy-11α-isopropylthioprostaglandin $E_2$ |
| 9 | prostaglandin $A_1$ | methanethiol | B | 11-deoxy-11α-methylthioprostaglandin $E_1$ |
| 10 | prostaglandin $A_1$ | 1-butanethiol | B | 11-deoxy-11α-butylthioprostaglandin $E_1$ |
| 11 | 13,14-dihydroprostaglandin $A_1$ | methanethiol | B | 11-deoxy-11α-methylthio-13,14-dihydroprostaglandin $A_1$ |
| 12 | 13,14-dihydroprostaglandin $A_1$ | 1-propanethiol | B | 11-deoxy-11α-propylthio-13,14-dihydroprostaglandin $A_1$ |

EXAMPLE 13

Preparation of 11-deoxy-11α/β-acetylthio-15-O-acetylprostaglandin $E_2$ methyl ester A solution of 5 g. of the methyl ester of 15-O-acetylprostaglandin $A_2$ in 10 ml. of thioacetate acid is refluxed three hours. The solution is evaporated in vacuo at 45° C. and the residue is dissolved in benzene and the solution evaporated in vacuo to afford 5.18 g. of an oil. Thin layer chromatography indicates two compounds (epimers at C-11); λ max 1735 $cm^{-1}$ (saturated carbonyls), 1700 $cm^{-1}$

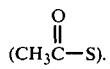

EXAMPLES 14-16

Treatment of the following A type prostaglandins with thiolacetic acid by the procedure of Example 13 affords the 11-acetylthio E-type prostaglandins of the following table.

| Example | Starting Prostaglandin-A | Product 11-acetylthio-prostaglandin E |
|---|---|---|
| 14 | Prostaglandin $A_2$ | 11-deoxy-11α/β-acethylthioprostaglandin $E_2$ |
| 15 | Prostaglandin $A_1$ | 11-deoxy-11α/β-acetylthioprostaglandin $E_1$ |
| 16 | 13,14-dihydroprostaglandin $A_1$ | 11-deoxy-11α/β-acetylthio-13,14-dihydroprostaglandin $E_1$ |

EXAMPLE 17

Preparation of 11-deoxy-11α-methyl-15-deoxy-15-mehylprostaglandin $E_2$ methyl ester To a solution, maintained at $-10°$ C., of lithium dimethyl cuprate (4.87 g. cuprous iodide in 10 cc ether titrated with 2M methyllithium until the solution is clear) is added dropwise a solution of 5.0 g. of the methyl ester of 15-O-acetyl-prostaglandin $A_2$ in 25 ml. of ether. The solution is stirred for 15 minutes and then is added to 200 ml. of saturated aqueous ammonium chloride. The aqueous solution is extracted with ether. The ether extracts are combined, washed with brine, dried with anhydrous magnesium sulfate and evaporated in vacuo to yield 4.65 g. of an oil. The oil is purified by silica gel chromatography with 3% ethyl acetate/benzene to afford 2.56 g. of the product as an oil; λ max 1740 cm$^{-1}$ (saturated carbonyls); $[α]_D^{25} = -75.4°$ (C = 0.5, chloroform) in addition is obtained 11-deoxy-11α-methyl-15-Q-acetylprostaglandin $A_2$ methyl ester.

EXAMPLE 18

Preparation of 11-deoxy-11α-methyl-prostaglandin $E_2$ methyl ester

To a $-20°$ C. solution of lithium dimethyl cuprate (prepared from 3.9 gm. cuprous iodide in ten ml. ether by titration with 1 M methyllithium until the resulting solution is clear) is added a solution of 3.36 g. of the methyl ester of prostaglandin $A_2$ (Example 4) in ten ml. of ether. The resulting solution is stirred forty-five minutes and then poured into 250 ml. of saturated ammonium chloride and stirred 15 minutes. The solution is extracted with ether and the ether extracts are combined, washed with brine, dried with anhydrous magnesium sulfate and evaporated in vacuo to afford 3.37 g. of an oil that is homogenous by thin layer chromatography; λ max 3400 cm$^{-1}$ (hydroxyl), 1740 (saturated carbonyls); $[α]_D^{25} = -47.8°$ (C = 0.5, chloroform).

EXAMPLE 19

Preparation of 11-deoxy-11α-vinylprostaglandin $E_2$ methyl ester

To a solution of (17.5 mM) lithium divinyl cuprate (prepared from 6.87 g. of the cuprous iodide-tributylphosphine complex and 17.5 ml. of 2 molar vinyllithium) in tetrahydrofuran at $-78°$ C. is added a solution of 3 g. (8.65 mM) of prostaglandin $A_2$ methyl ester (Example 4) in 10 ml. of ether. The resulting viscous solution is diluted with 10 ml. of tetrahydrofuran and stirred at $-78°$ C. for 60 minutes.

The solution is poured into 150 ml. of saturated aqueous ammonium chloride and stirred 1 hour at room temperature with 200 ml. of ether. The ether solution is separated and is extracted with water, washed with brine, dried with magnesium sulfate and evaporated in vacuo to yield 12.1 gm. of an oil.

The oil is triturated with methanol several times and the methanol washes are combined, filtered through celite and evaporated in vacuo to afford 5.9 g. of an oil; λ max: 3400 cm$^{-1}$ (hydroxyl), 1740 cm$^{-1}$ (saturated ketone and ester), 1635 cm$^{-1}$ (vinyl group); 970 cm$^{-1}$ (trans double bond), 920 cm$^{-1}$ (terminal vinyl).

EXAMPLES 20-28

Treatment of the A-type prostaglandin methyl esters listed in the table below with the indicated organolithium cuprates and by the indicated procedure is productive of the 11-alkyl or 11-alkenyl E-type prostaglandins of the table.

| Example | Cuprate Reagent | Method of Example | Starting Prostaglandin Ester | Product 11α-alkyl/alkenyl-11-deoxyprostaglandin-E |
|---|---|---|---|---|
| 20 | diethylcopperlithium | 18 | prostaglandin $A_2$ methyl ester | 11-deoxy-11α-ethylprostaglandin $e_2$ methyl ester |
| 21 | dipropylcopperlithium | 18 | prostaglandin $A_2$ methyl ester | 11-deoxy-11α-propylprostaglandin $E_2$ methyl ester |
| 22 | diisopropylcopperlithium | 18 | prostaglandin $A_2$ methyl ester | 11-deoxy-11α-isopropylprostaglandin $E_2$ methyl ester |
| 23 | dipropenylcopperlithium | 19 | prostaglandin $A_2$ methyl ester | 11-deoxy-11α-propenylprostaglandin $E_2$ methyl ester |
| 24 | dimethylcopperlithium | 18 | prostaglandin $A_1$ methyl ester | 11-deoxy-11α-methylprostaglandin $E_1$ methyl ester |
| 25 | diethylcopperlithium | 18 | prostaglandin $A_1$ methyl ester | 11-deoxy-11α-ethylprostaglandin $E_1$ methyl ester |
| 26 | divinylcopperlithium | 19 | prostaglandin $A_1$ methyl ester | 11-deoxy-11α-vinylprostaglandin $E_1$ methyl ester |
| 27 | dipropenylcopperlithium | 19 | prostaglandin $A_1$ methyl ester | 11-deoxy-11α-propenylprostaglandin $E_1$ methyl ester |
| 28 | divinylcopperlithium | 19 | 13,14-dihydroprostaglandin $A_1$ methyl ester | 11-deoxy-11α-vinyl-13,14-dihydroprostaglandin $E_1$ methyl ester |

EXAMPLE 29

Preparation of 11-deoxy-11α-methyl-13,14-dihydroprostaglandin $E_1$

To a suspension of 300 mg. of 5% rhodium-on-carbon in 10 ml. of ethylacetate is added a solution of 1.02 g. of 11-deoxy-11α-methylprostaglandin $E_2$ (Example 57) in 10 ml. ethylacetate. The resulting suspension is hydrogenated at 50 psi of hydrogen for 1 hour. The solution is filtered and the solvent is evaporated in vacuo to afford 1.04 g. of an oil. The oil is purified by dry column chromatography on a 29" × 1½" flat diameter nylon tube filled with acid washed silica gel. The column is developed with ethyl acetate/benzene/acetic acid (10:40:1) and the section corresponding to rf = 0.38–0.53 was eluted with 20% methanol in chloroform to afford 542 mg. of the product as an oil; λ max 3400 cm$^{-1}$ (carboxyl and hydroxyl), 1740–1710 cm$^{-1}$ (carboxyl and saturated ketone); $[\alpha]_D^{25} = -49.5$ (C = 0.8, chloroform).

EXAMPLES 30–32

Treatment of the 11-deoxy-11-alkylprostaglandin $E_2$ methyl esters listed in the table below by the procedure of Example 29 yields the 11α-alkyl-11-deoxy-13,14-dihydro-prostaglandins $E_1$ of the table.

| Example | Starting Prostaglandin-$E_2$ | Product - 11α-alkyl-11-deoxy-13,14-dihydroprostaglandin-$E_1$ |
|---|---|---|
| 30 | 11-deoxy-11α-ethyl-prostaglandin $E_2$ | 11-deoxy-11α-ethyl-13,14-dihydroprostaglandin $E_1$ |
| 31 | 11-deoxy-11α-propyl-prostaglandin $E_2$ | 11-deoxy-11α-propyl-13,14-dihydroprostaglandin $E_1$ |
| 32 | 11-deoxy-11-isopropylprostaglandin $E_2$ | 11-deoxy-11α-isopropyl-13,14-dihydroprostaglandin $E_1$ |

EXAMPLE 33

Preparation of 11-deoxy-11α-dicarboethoxymethyl-15-O-acetylprostaglandin $E_2$ methyl ester To a solution of 97 mg. of the methyl ester of 15-O-acetyl-prostaglandin $A_2$ and 44 mg. of diethylmalonate in one ml. of tetrahydrofuran is added one drop of a 35% solution of benzyltrimethyl ammonium hydroxide in methanol. Two ml. of tetrahydrofuran is added and the solution is stirred overnight.

The solution is applied directly to a 2 mm silica-gel thin layer chromatography plate and developed with 20% ethyl acetate/benzene. The band corresponding to the product is scraped off of the plate and the product is isolated by elution off of the silica with 20% methanol/chloroform. The resulting solution is evaporated to afford 76 mg. of an oil; λ max 1740 cm$^{-1}$ (saturated carbonyls), 1225 cm$^{-1}$ (OAc), 1180 and 1020 cm$^{-1}$ (CO$_2$Et), $[\alpha]_D^{25} = -60.98°$ (C = 0.305, chloroform).

EXAMPLE 34

Preparation of 11-deoxy-11α-(α,α-dicarboethoxy)methylprostaglandin $E_2$

To a solution of 11-deoxy-11α-(α,α-dicarboethoxy)-methyl-15-O-acetyl-prostaglandin $E_2$ methyl ester (Example 33) in methanol is added 2.2 equivalents of a 2.5N aqueous sodium hydroxide solution. The resulting solution is stirred for 4 hours and then poured into water. Extraction of the aqueous solution with ether removes unreacted ester. The aqueous solution is acidified and extracted with ether. The ether solution is washed with brine, dried with magnesium sulfate and evaporated in vacuo to afford the product. Purification via dry column chromatography affords pure 11-deoxy-11α-(α,α-dicarboethoxy)methylprostaglandin $E_2$.

EXAMPLE 35

Preparation of 11-deoxy-11α-(α,α-dicarboxy)methylprostaglandin $E_2$

To the product derived from the treatment of 5.5 g. of 15-O-acetyl-prostaglandin $A_2$ methyl ester with diethylmalonate as per Example 33, in 25 ml. of tetrahydrofuran is added 30 ml. of 2.5N aqueous sodium hydroxide. The solution is stirred overnight at room temperature, and is then heated at 80° C. for one hour. The cooled solution is poured into 50 cc ether and 100 cc water. The aqueous phase is separated and extracted with ether.

The aqueous phase is acidifed with 6N aqueous hydrochloric acid, saturated with sodium chloride and extracted with ether. The ether solution is dried with magnesium sulfate and evaporated in vacuo to afford 4.48 g. of nearly pure product; λ max 3400–2600 cm$^{-1}$ (carboxyl and hydroxyl groups), 1710–1750 cm$^{-1}$ (saturated ketone and carboxyls).

EXAMPLES 36–38

Treatment of the indicated A-type prostaglandins with the designated malonates by the procedure of Example 33 furnishes the products of the table.

| Example | Reagent Malonate | Starting Prostaglandin A | Product Prostaglandin E |
|---|---|---|---|
| 36 | α-methyldiethylmalonate | 15-O-acetylprostaglandin $A_2$ methyl ester | 11-deoxy-11α-(α,α-dicarboethoxy ethyl-15-O-acetyl-prostaglandin $E_2$ methyl ester |
| 37 | α-ethyldiethylmalonate | 15-O-acetylprostaglandin $A_2$ methyl ester | 11-deoxy-11α-(α,α-dicarboethoxy propyl-15-O-acetyl-prostaglandin $E_2$ methyl ester |
| 38 | diethylmalonate | prostaglandin $A_1$ methyl ester | 11-deoxy-11α-(α,α-dicarboethoxy methylprostaglandin $E_1$ methyl ester |

EXAMPLE 39

Preparation of 11-deoxy-11α-nitromethyl-15-O-acetylprostaglandin $E_2$ methyl ester To a solution of 15.1 g. of the methyl ester of 15-O-acetylprostaglandin $A_2$ in 15 ml. of tetrahydrofuran is added a solution of 15 ml. nitromethane containing 1 ml. of a 35% solution of triton B (benzyl-trimethyl ammonium hydroxide) in methanol. The solution is stirred for one hour and is then poured into a mixture of 75 ml. of water and 70 ml. of ether. One ml. of 6N aqueous hydrochloric acid is added and the aqueous layer is extracted with ether. The ether extracts are combined, washed with brine, dried (anhydrous magnesium sulfate) and evaporated in vacuo to afford 17.5 g. of an oil that can be purified by dry column chromatography; λ max 1740 cm$^{-1}$ (saturated carbonyls), 1555 cm$^{-1}$ (NO$_2$), 1375 cm$^{-1}$ (NO$_2$), 1225 cm$^{-1}$ (OAc), $[\alpha]_D^{25} = -45.5$, (C = 0.530, chloroform).

EXAMPLES 40–45

Treatment of the indicated A-type prostaglandins with the designated nitroalkanes via the procedure of Example 39 is productive of the products of the following table.

| Ex. | Reagent Nitroalkane | Starting Prostaglandin A | Product - 11-deoxy-11α-(nitroalkyl)-prostaglandin E |
|---|---|---|---|
| 40 | nitroalkane | 15-O-acetylprostaglandin $A_2$ methyl ester | 11-deoxy-11α-(α-nitroethyl)-15-O-acetylprostaglandin $E_2$ methyl ester |
| 41 | 2-nitropropane | 15-O-acetylprostaglandin $A_2$ methyl ester | 11-deoxy-11α-(α-nitro, α-methylethyl)-15-O-acetylprostaglandin $E_2$ methyl ester |
| 42 | 1-nitropropane | 15-O-acetylprostaglandin $A_2$ methyl ester | 11-deoxy-11α-(α-nitropropyl)-15-O-acetylprostaglandin $E_2$ methyl ester |
| 43 | nitromethane | prostaglandin $A_1$ methyl ester | 11-deoxy-11α-nitromethyl prostaglandin $E_1$ methyl ester |
| 44 | nitroethane | prostaglandin $A_1$ methyl ester | 11-deoxy-11α-(α-nitroethyl)prostaglandin $E_1$ methyl ester |
| 45 | nitromethane | 13,14-dihydroprostaglandin $A_1$ methyl ester | 11-deoxy-11α-nitromthyl-13,14-dihydroprostaglandin $E_1$ methyl ester |

EXAMPLE 46

Preparation of 11-deoxyprostaglandin $E_2$ methyl ester

To a suspension of 300 mg. potassium carbonate in 30 ml. of methanol is added 11-deoxy-15-O-acetyl-prostaglandin $E_2$ methyl este (Example 96) in one ml. of methanol. The solution is stirred for 48 hours and is then acidified with 6N aqueous hydrochloric acid. The solution is diluted with water and extracted with ether. The ether solution is washed with brine, dried with magnesium sulfate and evaporated in vacuo to yield 540 mg. of crude product. The product is purified by dry column chromatography using acid washed silica gel and eluting with 20% ethylacetate in benzene: λ max: 3400 cm$^{-1}$ (hydroxyl), 1735 cm$^{-1}$ (saturated ketone and ester).

EXAMPLE 47

Preparation of 11-deoxy-11α-nitromethyl prostaglandin $E_2$

To a solution of 11.54 g. of the methyl ester of 11-deoxy-11α-nitromethyl-15-O-acetyl-prostaglandin $E_2$ (Example 39) in 40 ml. of methanol is added 45 ml. of a 2.5N sodium hydroxide solution and the resulting solution is stirred at room temperature for 2 hours. The solution is poured into 100 ml. of ether and 100 ml. of water. The aqueous layer is separated and extracted with ether. The aqueous layer is covered with ether and acidified with 23 ml. of 6N aqueous hydrochloric acid. The acidic solution is saturated with sodium chloride and extracted with ether. The ether is dried with magnesium sulfate and evaporated in vacuo to give 10.3 g. of a viscous oil that is purified by dry column chromatography on acid washed silica gel; λ max 3600–3400 cm$^{-1}$ (hydroxyl and carboxyl), 1735 cm$^{-1}$ (saturated carbonyl), 1700 cm$^{-1}$ (carboxyl), 1550 cm$^{-1}$ (nitro); $[α]_D^{25}$ = −41.5° (C = 1.0, chloroform).

EXAMPLES 48–67

Saponification of the prostaglandin esters listed in the table by the indicated procedures yields the product prostaglandin acids of the following table.

| Ex. | Starting Prostaglandin Ester | Method Of | Product Acid |
|---|---|---|---|
| 48 | Example 36 | Example 34 | 11-deoxy-11α-(α,α-dicarboethoxyethyl)prostaglandin $E_2$ |
| 49 | Example 37 | Example 34 | 11-deoxy-11α-(α,α-dicarboethoxypropyl)-prostaglandin $E_2$ |
| 50 | Example 38 | Example 34 | 11-deoxy-11α-(α,α-dicarboethoxymethyl)-prostaglandin $E_1$ |
| 51 | Example 40 | Example 47 | 11-deoxy-11α-(α-nitroethyl)prostaglandin $E_2$ |
| 52 | Example 41 | Example 47 | 11-deoxy-11α-(α-nitro, α-methylethyl)prostaglandin $E_2$ |
| 53 | Example 42 | Example 47 | 11-deoxy-11α-(α-nitropropyl)prostaglandin $E_2$ |
| 54 | Example 43 | Example 47 | 11-deoxy-11α-nitromethyl prostaglandin $E_1$ |
| 55 | Example 44 | Example 47 | 11-deoxy-11α-(α-nitroethyl)prostaglandin $E_1$ |
| 56 | Example 45 | Example 47 | 11-deoxy-11α-nitromethyl-13,14-dihydroprostaglandin $E_1$ |
| 57 | Example 18 | Example 47 | 11-deoxy-11α-methylprostaglandin $E_2$ |
| 58 | Example 19 | Example 47 | 11-deoxy-11α-vinylprostaglandin $E_2$ |
| 59 | Example 20 | Example 47 | 11-deoxy-11α-ethylprostaglandin $E_2$ |
| 60 | Example 21 | Example 47 | 11-deoxy-11α-propylprostaglandin $E_2$ |
| 61 | Example 22 | Example 47 | 11-deoxy-11α-isopropylprostaglandin $E_2$ |
| 62 | Example 23 | Example 47 | 11-deoxy-11α-propenylprostaglandin $E_2$ |
| 63 | Example 24 | Example 47 | 11-deoxy-11α-methylprostaglandin $E_1$ |
| 64 | Example 25 | Example 47 | 11-deoxy-11α-ethylprostaglandin $E_1$ |
| 65 | Example 26 | Example 47 | 11-deoxy-11α-vinylprostaglandin $E_1$ |
| 66 | Example 27 | Example 47 | 11-deoxy-11α-propenylprostaglandin $E_1$ |
| 67 | Example 28 | Example 47 | 11-deoxy-11α-vinyl-13,14-dihydroprostaglandin $E_1$ |

EXAMPLE 68

Preparation of 11α/11β-cyano-11-deoxy-15-O-acetyl-prostaglandin $E_2$ methyl ester To a solution of 9.4 g. of the methyl ester of 15-O-acetyl-prostaglandin-$A_2$ in a mixture of 10 ml. acetonecyanohydrin and 10 ml. methanol is added 1 ml. of 5% aqueous sodium carbonate. The resulting solution is refluxed overnight and after cooling, poured into cold water and extracted with ether. The combined ether extracts are washed with brine and dried with anhydrous magnesium sulfate and evaporated in vacuo to give 12.3 g. of an oil.

The material is redissolved in benzene and washed with water to remove acetonecyanohydrin. The benzene solution is dried with magnesium sulfate and evaporated in vacuo. The material is purified by dry column chromatography to afford 8.5 g. of subject compound as an oil; λmax 2220 cm$^{-1}$ (nitrile), 1735 cm$^{-1}$ (saturated carbonyls); $[α]_D^{25}$ = −56.23°, (C = 0.918, chloroform).

EXAMPLES 69–70

Treatment of the listed A-type prostaglandins by the procedure of Example 68 is productive of the 11α/β-cyano products of the following table.

| Example | Starting Prostaglandin-A | Product 11α/β-11-deoxy-prostaglandin-E |
|---|---|---|
| 69 | prostaglandin A₁ methyl ester | 11α/β-cyano-11-deoxyprostaglandin E₁ methyl ester |
| 70 | 13,14-dihydroprostaglandin A₁ methyl ester | 11α/β-cyano-11-deoxy-13,14-dihydroprostaglandin E₁ methyl ester |

EXAMPLE 71

Preparation of 11α/β-cyano-11-deoxy-prostaglandin E₂

To a solution of 3 g. of the methyl ester of 11α/β-cyano-11-deoxy-15-O-acetyl-prostaglandin E₂ (Example 68) in 36 ml. of methanol is added 12 ml. of an aqueous saturated solution of sodium cyanide. The solution is stirred for 96 hours and then poured into 100 ml. of ether. 20 ml. of water is added and the ether is extracted twice with 15 ml. 5% aqueous sodium bicarbonate. The combined aqueous extracts are acidified to pH 3 with 6N aqueous hydrochloric acid, saturated with sodium chloride, and extracted with ether. The ether extracts are combined, dried with magnesium sulfate, and evaporated in vacuo to afford 1.64 g. of 11α/β-cyano-11-deoxyprostaglandin E₂ as an oil; λmax 3400 cm⁻¹ (carboxyl, hydroxyl), 2220 cm⁻¹ (nitrile), 1735 cm⁻¹ (saturated carbonyl), 1700 cm⁻¹ (carboxyl).

The first ether extract is dried with magnesium sulfate and evaporated in vacuo to afford 0.8 g. of 11α/β-cyano-11-deoxyprostaglandin E₂ methyl ester as an oil; λmax 3400 cm⁻¹ (hydroxyl), 2220 cm⁻¹ (nitrile), 1735 cm⁻¹ (saturated carbonyl, ester).

EXAMPLES 72-73

Ester hydrolysis of the following compounds by this procedure of Example 71 yields the products of the following table.

| Example | Starting Prostaglandin | Product 11α/β-cyano-11-deoxyprostaglandin E |
|---|---|---|
| 72 | Example 69 | 11α/β-cyano-11-deoxyprostaglandin E₁ |
| 73 | Example 70 | 11α/β-cyano-11-deoxy-13,14-dihydroprostaglandin E₁ |

EXAMPLE 74

Preparation of 11α/β-carboxamido-11-deoxy-15-O-acetyl prostaglandin E₂ methyl ester To a solution of 5.04 g. of the methyl ester of 11α/β-cyano-11-deoxy-15-O-acetylprostaglandin E₂ (Example 68) in 10 ml. of ethanol, 10 ml. tetrahydrofuran and 10 ml. cyclohexene is added a solution consisting of 1.5 ml. of 25% methanolic tetramethylammonium hydroxide in 7.0 ml. of 30% hydrogen peroxide. The resulting solution is heated to 60° C. for one hour and then stirred 48 hours at room temperature. One drop of methyltricaprylammonium chloride is added and the solution is heated for 2 hours at 55° C. The solution is cooled and poured into 100 ml. ether and 100 ml. water. The aqueous layer is extracted with ether. The ether extracts are combined, dried with anhydrous magnesium sulfate and evaporated in vacuo to give 4.96 g. of an oil. The oil is purified by dry column chromatography on a 20″ × 1/4″ column of silica gel and developed with 20% ethyl acetate in benzene to give 2.5 g. of the product carboxamide as an oil; λmax 3400–3600 cm⁻¹ (NH₂ of carboxamide), 1735 cm⁻¹ (saturated ketone and esters), 1675 cm⁻¹ (carboxamide carbonyl), 1620 cm⁻¹ (carboxamide), 1220 cm⁻¹ (acetate), 1180 cm⁻¹ (methyl ester); $[\alpha]_D^{25} = -114.7°$ (C = 0.63, chloroform).

EXAMPLE 75

Preparation of 11α-carboxamido-11-deoxyprostaglandin E₂

To a solution of 1.41 g. of 11α/β-carboxamido-11-deoxy-15-O-acetylprostaglandin E₂ methyl ester (Example 74) in 5 ml. of methanol is added 2.8 ml. of a 2.5N aqueous sodium hydroxide solution and 2.2 ml. of water. The solution is stirred overnight and poured into 50 ml. of ether and 50 ml. of water. The water is extracted with ether and the ether solutions are discarded. The aqueous solution is acidified to pH 2 with 6N aqueous hydrochloric acid and saturated with sodium chloride. The aqueous solution is extracted with ether; the ethereal solution is dried with magnesium sulfate and the ether is evaporated in vacuo to yield 1.1 g. of the product as an oil; λmax: 3400 cm⁻¹ (carboxyl, hydroxyl, and amido hydrogens), 1740 cm⁻¹ (saturated ketone), 1710 cm⁻¹ (amide carbonyl); $[\alpha]_D^{25} = -25°$ (C = -76 chloroform, acetone).

EXAMPLE 76

Preparation of 11α-carboxy-11-deoxyprostaglandin E₂

To a solution of 737 mg. of 11α-carboxamido-11-deoxy-15-O-acetylprostaglandin E₂ methyl ester (Example 74) in 5 ml. of methanol is added dropwise 5 ml. of a 2.5N aqueous sodium hydroxide solution. The solution is heated at 80° C. for two hours and an additional 5 ml. of 2.5N aqueous sodium hydroxide then is added and the solution is heated at 80° C. for 15 hours. The solution is cooled and extracted with ether. The aqueous solution is acidified with 6N aqueous hydrochloric acid and extracted with ether. The ethereal solution is washed with brine, dried with magnesium sulfate and evaporated in vacuo to yield 520 mg. of the crude product; λmax: 3400–2700 cm⁻¹ (hydroxyl and carboxyl groups), 1740–1710 cm⁻¹ (saturated ketone and carboxyl groups).

EXAMPLES 77-79

Hydrogenation of the listed prostaglandin E₂ derivative by the procedure of Example 29 furnishes the product 13,14-dihydroprostaglandin E₁ of the following table.

| Example | Starting 11-substituted prostaglandin E₂ | Product 11-substituted-13,14-dihydroprostaglandin E₁ |
|---|---|---|
| 77 | Example 74 | 11α/β-carboxamido-11-deoxy-13,14-dihydro-15-O-acetyl prostaglandin E₁ methyl ester |
| 78 | Example 75 | 11α-carboxamido-11-deoxy-13,14-dihydroprostaglandin E₁ |
| 79 | Example 76 | 11α-carboxy-11-deoxy-13,14-dihydroprostaglandin E₁ |

EXAMPLE 80

Preparation of 11-deoxy-11α-methyl-prostaglandin $F_{2\alpha}$

To a $-78°$ C. solution of 877 mg. 11-deoxy-11α-methylprostaglandin $E_2$ (Example 57) in 8 ml. tetrahydrofuran is added 9.8 ml. of 0.66M lithium perhydro-9-b-boraphenalyl hydride in tetrahydrofuran. The solution is stirred for 30 minutes and then 15 ml. of water is added and the dry-ice bath is removed. The solution is poured into 20 ml. of water and extracted with ether. The combined ether extracts are washed with 5% sodium bicarbonate. The combined aqueous solutions are acidified with 6N hydrochloric acid, saturated with sodium chloride and extracted with ether. The ether is dried with anhydrous magnesium sulfate and evaporated in vacuo to an oil; λmax 3400 cm$^{-1}$ (OH), 1700 cm$^{-1}$ (COOH); 420 Hz (2H) 15-H and 9β-H; $[\alpha]_D^{25} = +15°$ (C = 0.4, chloroform).

EXAMPLE 81

Preparation of 11α-carboxamido-11-deoxyprostaglandin $F_{2\alpha}$

To a $-78°$ C. solution of 1.59 g. of the methyl ester of 11α-carboxamido-11-deoxy-15-O-acetyl-prostaglandin $E_2$ (Example 75) in 10 ml. tetrahydrofuran is added 7.35 ml. of 0.65M lithium perhydro-9-b-boraphenalyl hydride in tetrahydrofuran. The solution is stirred for 60 minutes at $-78°$, then stirred at room temperature for 20 minutes. The tetrahydrofuran is evaporated in vacuo at 25° C. The residue is dissolved in 2 ml. methanol, 6 ml. water and 4 ml. of 2.5N aqueous sodium hydroxide and stirred 3 hours at room temperature. The solution containing the 11-carboxamido-11-deoxy-15-O-acetyl-prostaglandin $E_2$ methyl ester is poured into 50 ml. of water and extracted with ether. The ether solution is washed with 5% aqueous sodium bicarbonate and combined with the aqueous solution. The combined aqueous solution is acidified with 6N aqueous hydrochloric acid, saturated with sodium chloride, and extracted with ether. The ether is dried with magnesium sulfate and evaporated in vacuo to afford 1.48 g. of a viscous oil; λmax, 3400 cm$^{-1}$ (OH, NH$_2$, COOH), 1700 cm$^{-1}$ (COOH), 1660 cm$^{-1}$ (CONH$_2$); 405 Hz (15-H, 9β-H); $[\alpha]_D^{25} = +8.2°$ (C = 0.65, chloroform.

EXAMPLES 82–89

Carbonyl reduction of the listed prostaglandin E derivatives by the procedure of the example designated furnishes the product prostaglandin $F_\alpha$, of the following table.

| Example | Starting 11-substituted prostaglandin E | Method | Product 11-substituted-prostaglandin $F_\alpha$ |
|---|---|---|---|
| 82 | Example 21 | 81 | 11α-propyl-11-deoxyprostaglandin $F_{2\alpha}$ |
| 83 | Example 22 | 81 | 11α-isopropyl-11-deoxyprostaglandin $F_{2\alpha}$ |
| 84 | Example 6 | 80 | 11α-methylthio-11-deoxyprostaglandin $F_{2\alpha}$ |
| 85 | Example 39 | 81 | 11α-nitromethyl-11-deoxyprostaglandin $F_{2\alpha}$ |
| 86 | Example 35 | 80 | 11α-dicarboxymethyl-11-deoxyprostaglandin $F_{2\alpha}$ |
| 87 | Example 25 | 81 | 11α-ethyl-11-deoxyprostaglandin $F_{1\alpha}$ |
| 88 | Example 38 | 81 | 11α-(α,α-dicarboethoxy)-methyl-11-deoxyprostaglandin $F_{1\alpha}$ |
| 89 | Example 29 | 80 | 11α-methyl-11-deoxy-13,14-dihydroprostaglandin $F_{1\alpha}$ |

EXAMPLE 90

Conversion of 11α-methyl-11-deoxyprostaglandin $E_2$ to 11α-methyl-11-deoxyprostaglandin $F_{2\alpha}$ and 11α-methyl-11-deoxyprostaglandin $F_{2\beta}$ To a solution of 11α-methyl-11-deoxyprostaglandin $E_2$ in methanol at 0° C. is added 1 molar equivalent of sodium borohydride. After 60 minutes the solution is poured into water, acidified to pH=3 with 6N hydrochloric acid, saturated with sodium chloride and extracted with ether. The ethereal solution is dried with magnesium sulfate and the ether is evaporated in vacuo to afford a mixture of 11α-methyl-11-deoxyprostaglandin $F_{2\alpha}$ and 11α-methyl-11-deoxyprostaglandin $F_{2\beta}$.

EXAMPLES 91–95

Carbonyl reduction of the listed 11-substituted prostaglandin (E type) by the method of Example 90 is productive of the 11-substituted prostaglandins (F type) of the table.

| Example | Starting 11-substituted prostaglandin | Product 11-substituted prostaglandin $F\alpha/\beta$ |
|---|---|---|
| 91 | Example 29 | 11α-methyl-11-deoxy-13,14-dihydroprostaglandin $F_{1\alpha}/F_{1\beta}$ |
| 92 | Example 51 | 11α-)α-nitroethyl)-11-deoxyprostaglandin $F_{2\alpha}/F_{2\beta}$ |
| 93 | Example 65 | 11α-vinyl-11-deoxyprostaglandin $F_{1\alpha}/F_{1\beta}$ |
| 94 | Example 75 | 11α-carboxamido-11-deoxyprostaglandin $F_{2\alpha}/F_{2\beta}$ |
| 95 | Example 66 | 11α-propenyl-11-deoxyprostaglandin $F_{1\alpha}/F_{1\beta}$ |

EXAMPLE 96

Preparation of 11-deoxyprostaglandin $E_2$ from 15-O-acetyl prostaglandin $A_2$ methyl ester To a solution of 1.04 g. of 15-O-acetylprostaglandin $A_2$ methyl ester in 5 ml. of methanol is added a solution of 209 mg. of sodium cyanoborohydride in 2 ml. of methanol. The solution is adjusted to pH 3 with 2N methanolic hydrogen chloride and maintained at this pH by addition of methanolic hydrochloric acid as necessary. After 90 minutes the solution is evaporated in vacuo, 5 ml. of water is added. The solution is saturated with sodium chloride and extracted with ether. The ether extracts are dried with magnesium sulfate and evaporated in vacuo to yield 1.02 g. of an oil consisting mainly of 11-deoxy-15-O-acetyl-prostaglandin $F_{2\alpha}/F_{2\beta}$ methyl esters.

To a solution of 900 mg. of the above mixture of 11-deoxy-15-O-acetyl-prostaglandin $F_{2\alpha}/F_{2\beta}$ methyl esters in 30 ml. of acetone at 0° C. is added 0.8 ml. of a standard chromic acid solution. The solution is stirred 10 minutes and poured into 70 ml. of ice and water. The aqueous solution is extracted with ether. The ether solution is dried with magnesium sulfate and evaporated in vacuo to afford 830 mg. of 11-deoxy-15-O-acetyl-prostaglandin $E_2$ methyl ester as an oil.

To a solution of 11-deoxy-15-O-acetyl-prostaglandin $E_2$ methyl ester in methanol is added 4 equivalents of 2.5N aqueous sodium hydroxide. The solution is stirred for 3 hours, poured into water, saturated with sodium chloride and acidified with 6N aqueous hydrochloric acid to pH 3.

The acidic solution is extracted with ether. The ethereal extracts are dried with magnesium sulfate and evaporated in vacuo to afford 11-deoxyprostaglandin $E_2$; λmax: 3400–2700 cm$^{-1}$ (carboxyl and hydroxyl), 1745–1710 cm$^{-1}$ (saturated ketone and carboxyl groups).

EXAMPLE 97

Epimerization of 11-deoxyprostaglandin $E_2$ methyl ester

To a solution of 24 mg. of 11-deoxyprostaglandin $E_2$ methyl ester (Example 46) in 0.5 ml. of methylenechloride at $-5°$ C. is added 15 μl of triethylamine followed by 28 mg. of methanesulfonic acid anhydride in 0.5 cc methylenechloride. The solution is stirred at $-5°$ C. for 30 minutes and then all solvents are removed in vacuo.

The residue is dissolved in 5 ml. of ether and the ether solution is added to a flask containing 245 mg. of tetraethylammonium formate. The ether is evaporated in vacuo at $-5°$ C. and replaced by 2 cc of dry acetone. The solution is maintained at 10° C. for 18 hours. The acetone is removed in vacuo and the residue is dissolved in 10 cc ether. The ether solution is washed with 5 ml. of 5% aqueous sodium bicarbonate solution and 5 ml. of brine. The ether solution is dried with magnesium sulfate and the ether evaporated in vacuo to yield 26.7 mg. of 11-deoxy-15R-O-formylprostaglandin $E_2$ methyl ester as an oil.

Treatment of a solution of the 11-deoxy-15R-O-formylprostaglandin $E_2$ methyl ester in 0.5 ml. of methanol with a crystal of p-toluenesulfonic acid overnight yields 15R-11-deoxyprostaglandin $E_2$ methyl ester as an oil that chromatographs slightly ahead of the starting 15S-11-deoxyprostaglandin $E_2$ methyl ester on silica gel. The residue also contains some of the starting 15S material.

EXAMPLE 98

Racemization of 15S-11-deoxyprostaglandin $E_2$ methyl ester

To 13 mg. of 15S-11-deoxyprostaglandin $E_2$ methyl ester (Example 46) is added a solution of 5 mg. potassium carbonate in 0.5 ml. of 97% formic acid. The solution is stirred under nitrogen for 60 minutes. Benzene is added and the solution is evaporated in vacuo.

The residue is placed on a 2 mm silica gel plate and developed with 20% ethylacetate in benzene. The area corresponding to rf = 0.45–0.65 is removed and the compound is eluted off of the silica-gel with 20% methanol in chloroform. The silica-gel is filtered and the organic solvents are evaporated in vacuo to yield 9 mg. of a mixture of 11-deoxy-15-O-formylprostaglandin $E_2$ methyl ester and the corresponding 15R epimer.

The mixture of 15-O-formyl compounds is dissolved in 1 ml. of methanol and one small crystal of p-toluenesulfonic acid is added. The solution is stirred overnight to afford approximately a 1:1 mixture of 15S-11-deoxyprostaglandin $E_2$ methyl ester and 15R-11-deoxyprostaglandin $E_2$ methyl ester.

Thin layer chromatography on silica-gel indicates the newly formed epimer (15R) is slightly less polar than the starting (15S) epimer.

EXAMPLE 99

Conversion of 11-deoxy-11α-nitromethylprostaglandin $E_2$ to 11-deoxy-11-formylprostaglandin $E_2$ A solution of 208 mg. 11-deoxy-11α-nitromethylprostaglandin $E_2$ (Example 47) in 5.5 ml. of 0.21N aqueous sodium hydroxide is added dropwise to a very rapidly stirred solution of 0.5 ml. 6N hydrochloric acid in 5 ml. methanol. The solution is poured into 30 ml. of ether and 25 ml. of brine is added. The ether extracts are washed with brine, dried with magnesium sulfate and evaporated in vacuo to afford 167 mg. of a viscous oil. Purification by dry column chromatography using ethyl acetate/benzene/acetic acid for development followed by elution from the silica-gel with 20% methanol/chloroform affords the product as a mixture of 11-formyl-11-deoxyprostaglandin $E_2$ and the corresponding acetyl, 11-dimethoxymethyl-11-deoxyprostaglandin $E_2$.

EXAMPLE 100

Conversion of 11-deoxy-11α-(α,α-dicarboxy)methylprostaglandin $E_2$ to 11-deoxy-11α-carboxymethylprostaglandin $E_2$ A solution of 11-deoxy-11α-(α,α-dicarboxy)methylprostaglandin $E_2$ (Example 35) is dissolved in xylene and heated until carbon dioxide evolution begins. The solution is maintained at that temperature until the starting material has been consumed (thin layer chromatography evidence). The xylene solution is evaporated in vacuo to afford the product.

EXAMPLE 101

Preparation of 11α-(β-dimethylaminoethylthio)-11-deoxy-15-O-acetyl-prostaglandin $A_2$ methyl ester A solution of 164 mg. of 2-diethylaminoethanethiol hydrochloride in 1 ml. of methanol containing 6 drops of a 5% aqueous sodium bicarbonate solution (pH ~ 8) is added to a solution of 104 mg. 15-O-acetylprostaglandin $A_2$ methyl ester in 1 ml. of methanol. The solution is stirred twenty minutes and then evaporated in vacuo to a paste. The paste was dissolved in 20 ml. of ether and 20 ml. of water. A small amount of sodium chloride is added to break up the emulsion formed. The aqueous layer is extracted with ether. The ether extracts are dried with magnesium sulfate and the ether is evaporated in vacuo to afford the product as an oil; λmax: 1745 cm$^{-1}$ (saturated ketone and esters), 1240 cm$^{-1}$ (acetate).

EXAMPLE 102

Preparation of 11-thiol-15-O-acetylprostaglandin $F_{2α}$ methyl ester

To a solution of 1.0 g. of 11-acetylthio-11-deoxy-15-O-acetyl prostaglandin $A_2$ methyl ester in 4 ml. of tetrahydrofuran maintained at $-78°$ C. is added a solution of 0.65M lithium perhydro-9-b-boraphenalyl hydride in tetrahydrofuran. The solution is stirred at $-78°$ C. for 1 hour. The solution is then poured into 50 ml. of ether and 50 ml. of water and the aqueous layer is saturated with sodium chloride.

The aqueous layer is extracted with ether and the combined ether extracts are dried with magnesium sulfate and the ether is evaporated in vacuo to afford 1.7 g. of residue. Trituration of the residue with benzene/hexane followed by filtration and evaporation of the organic solvents affords 1.1 g. of crude product. The material is purified by partition chromatography to afford 150 mg. of 11-thiol-11-deoxy-15-O-acetyl prostaglandin $F_{2\alpha}$, methyl ester.

We claim:

1. A compound selected from the group consisting of those of the formula:

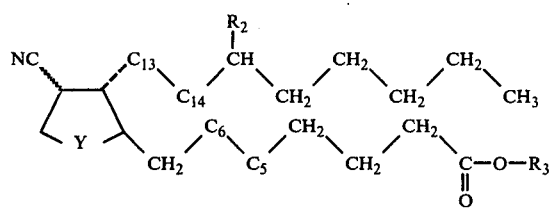

wherein $R_2$ is hydroxy, formyloxy, lower alkanoyloxy, lower alkylsulfonyloxy, tetrahydropyranyloxy, tri(-lower alkyl)-silyloxy or lower alkyl; $R_3$ is hydrogen or an alkyl group having from 1 to 12 carbon atoms; Y is a divalent radical selected from the group consisting of:

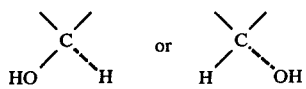

the moiety $-C_5-C_6-$ is ethylene or cis-vinylene and the moiety $-C_{13}-C_{14}-$ is ethylene or trans-vinylene; with the proviso that when $-C_5-C_6-$ is cis-vinylene then $-C_{13}-C_{14}-$ must be trans-vinylene; and the pharmaceutically acceptable salts cationic salts thereof when $R_3$ is hydrogen.

2. The optically active compound according to claim 1 wherein Y is the divalent radical:

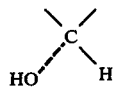

3. The optically active compound according to claim 1 wherein Y is the divalent radical:

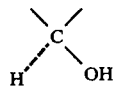

4. The optically active compound according to claim 2 wherein the 11-cyano moiety is in the alpha configuration.

5. The optically active compound according to claim 3 wherein the 11-cyano moiety is in the beta configuration.

6. A compound selected from the group consisting of those of the formula:

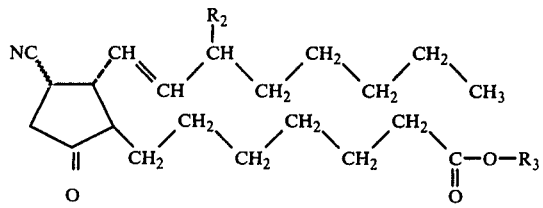

wherein $R_2$ is hydroxy, formyloxy, lower alkanoyloxy, lower alkylsulfonyloxy, tetrahydropyranyloxy, tri(-lower alkyl)-silyoxy or lower alkyl, $R_3$ is hydrogen or an alkyl group having from 1 to 12 carbon atoms; and the pharmaceutically acceptable cationic salts thereof when $R_3$ is hydrogen.

7. A compound selected from the consisting of those of the formula:

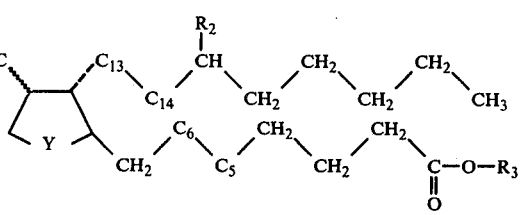

wherein $R_2$ is a lower alkyl group; $R_3$ is hydrogen or an alkyl group having from 1 to 12 carbon atoms; Y is a divalent radical of the formula

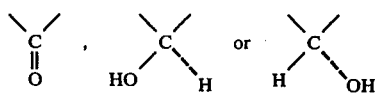

the moiety $C_5-C_6$ is ethylene or cis-vinylene and the moiety $C_{13}-C_{14}$ is ethylene or trans-vinylene with the proviso that when $-C_5-C_6$ is cis-vinylene then $-C_{13}-C_{14}$ is trans-vinylene; and the pharmaceutically acceptable salts thereof when $R_3$ is hydrogen.

8. The optically active compound according to claim 4 wherein $R_2$ is hydroxy, $R_3$ is hydrogen; 1-11α/β-cyano-11-deoxyprostaglandin $E_1$ having the following structural formula:

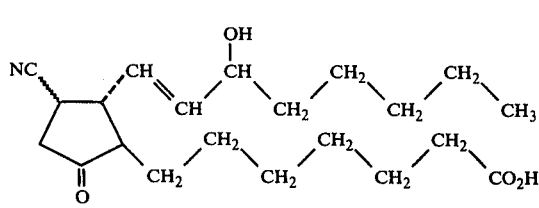

9. The optically active compound according to claim 4 wherein $R_2$ is hydroxy, $R_3$ is methyl; 1-11α/β-cyano-11-deoxyprostaglandin $E_1$ methyl ester having the following structural formula:

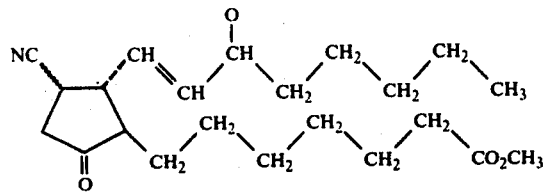

10. The optically active compound according to claim 2 wherein $R_2$ is hydroxy, $R_3$ is hydrogen,

[Y is

,]

$-C_5-C_6$ is cis-vinylene, $-C_{13}-C_{14}$ is trans-vinylene; 1–11α-cyano-11-deoxyprostaglandin $F_{2\alpha}$ having the following structural formula:

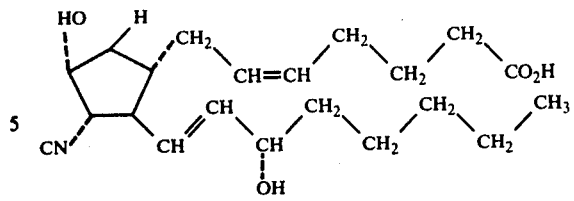

11. The optically active compound according to claim 3 wherein $R_2$ is hydroxy, $R_3$ is hydrogen,

[Y is

]

$-C_5-C_6-$ is cis-vinylene, $-C_{13}-C_{14}-$ is trans-vinylene; 1–11β-cyano-11-deoxyprostaglandin $-F_{2\beta}$ having the following structural formula:

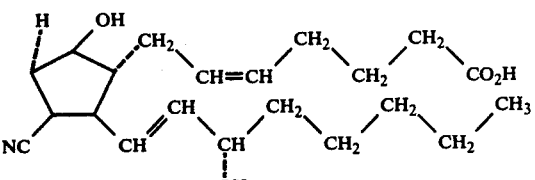

* * * * *